US00PP35384P2

(12) United States Plant Patent
Bedard

(10) Patent No.: US PP35,384 P2
(45) Date of Patent: Sep. 19, 2023

(54) HYBRID TEA ROSE PLANT NAMED 'WEKMAMOPRELA'

(50) Latin Name: *Rosa hybrida*
Varietal Denomination: WEKmamoprela

(71) Applicant: Early Morning LLC, Lawrenceburg, IN (US)

(72) Inventor: Christian Bedard, Rancho Cucamonga, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 17/803,749

(22) Filed: Nov. 9, 2022

(51) Int. Cl.
*A01H 5/02* (2018.01)
*A01H 6/74* (2018.01)

(52) U.S. Cl.
USPC ..... Plt./131
CPC ..... *A01H 6/749* (2018.05)

(58) Field of Classification Search
USPC ..... Plt./131
CPC ..... A01H 6/749; A01H 5/02
See application file for complete search history.

(56) References Cited

U.S. PATENT DOCUMENTS

PP4,437 P 7/1979 Warriner
PP14,398 P2 12/2003 Carruth

*Primary Examiner* — Keith O. Robinson
(74) *Attorney, Agent, or Firm* — McKee, Voorhees & Sease, PLC

(57) ABSTRACT

A new variety of Hybrid Tea rose suitable for garden decoration, having flowers of fuchsia pink with white reverse coloration.

1 Drawing Sheet

Classification: The present application relates to a new *Rosa hybrida* plant.

Variety denomination: The new plant has the varietal denomination 'WEKmamoprela'.

BACKGROUND OF THE INVENTION

This disclosure relates to a new and distinct variety of Hybrid Tea Rose. It has as its seed parent the variety known as 'WEKsunspat' (U.S. Plant Pat. No. 14,398) and as its pollen parent the variety known as 'SCRivo' (not patented). It was hybridized by Applicant.

SUMMARY OF THE INVENTION

Among the features which distinguish the new variety from other presently available and commercial rose cultivars known to Applicant are the following combinations of characteristics: its elegant high centered flower of fuchsia pink with white reverse coloration, its excellent color stability throughout the life of the flower, and its abundant blooms. The plant has an upright moderately spreading growing habit, suitable for outdoor garden decoration.

Asexual reproduction of the new variety by budding as performed in Kern County, Calif., shows that the foregoing and other distinguishing characteristics come true to form and are established and transmitted through succeeding asexual propagations. 'WEKmamoprela' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKsunspat' by the following combination of characteristics: whereas 'WEKmamoprela' bears double flowers (about 27 to 39 petals) of fuchsia pink with white reverse coloration, 'WEKsunspat' bears double flowers of soft apricot washed with green coloration with lesser petalage (about 23 to 30 petals). The new variety has an upright moderately spreading growing habit (about 100 to about 140 cm. in height), whereas the seed parent has a somewhat upright to moderately spreading significantly taller growing habit (about 160 to about 200 cm. in height).

The new variety may be distinguished from its pollen parent, 'SCRivo' by the following combination of characteristics: whereas 'WEKmamoprela' bears double flowers (about 27 to 39 petals) of fuchsia pink with white reverse coloration, 'SCRivo' bears double flowers of creamy white coloration with light apricot undertones and with significantly lesser petalage (about 25 petals). The new variety has an upright moderately spreading growing habit (about 100 to about 140 cm. in height), whereas the pollen parent has a bushy slightly spreading shorter growing habit (about 90 to about 120 cm. in height).

COMPARISON WITH THE CLOSEST COMMERCIALLY AVAILABLE CULTIVAR

The new variety may be distinguished from its closest commercially available cultivar, 'JACtwin' (U.S. Plant Pat. No. 4,437) by the following combination of characteristics: whereas 'WEKmamoprela' bears flowers of fuchsia pink with white reverse coloration, 'JACtwin' bears flowers of cherry and white bicolor coloration. The new variety has a moderate fruity fragrance with hints of spices, whereas the closest commercially available cultivar has no fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, Calif. in the month of October. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, Calif. in the month of October. Phenotypic expression may vary with environmental, cultural and climatic conditions, as well as differences in conditions of light and soil.

Flower

The new variety usually bears its flowers singly, sometimes in clusters of two to three per stem. Flowers may be borne in regular rounded clusters on medium to somewhat long stems (about 26 to about 65 cm.). The cluster ranges from about 17.0 to about 22.5 cm. in diameter. Outdoors, the plant blooms abundantly and nearly continuously during the growing season. The flowers have a moderate fruity fragrance with hints of spices.

Bud

The peduncle is about 2.8 to about 7.0 cm. in length, of average caliper (about 0.2 to about 0.5 cm. in diameter), and usually erect. It is almost entirely smooth, with very few stipitate glands, and few hairs. Peduncle color is between 146C and 146D sometimes lightly suffused, especially on the side exposed to the sun, with between 187B and 187A.

Before the calyx breaks, the bud is about 1.6 to about 2.2 cm. in diameter at the widest point, about 2.1 to about 2.5 cm. in length, and pointed to somewhat ovoid in shape. The surface of the bud bears between 7 to 11 foliaceous appendages with some hairs, usually with slender entire foliaceous parts extending beyond the tip of the bud about ½ or more of its length. Bud color is between 138A and 146C sometimes lightly suffused, especially on the side exposed to the sun, with between 187B and 187A.

The sepals are 5 per flower, about 2.0 to about 7.6 cm. in length and about 0.8 to about 1.2 cm. in width at the widest point. The outer surface color of the sepal is between 138A and 146C sometimes lightly suffused, especially on the side exposed to the sun, with between 187B and 187A. The outer surface of the sepal is smooth and bears between 0 to 4 foliaceous appendages with some hairs. The inner surface color of the sepal is near 146C broadly bordered by near 137B. After the sepals open, the inner surface color is often moderately suffused, especially on the area exposed to the sun, with between 187B and 187A. The inner surface of the sepal is covered with fine wooly tomentum; sepal margins are entire and lined with very few stipitate glands and some hairs. The sepals are moderately permanent, and usually straight in shape with acute apices.

The receptacle of the flower is of moderately short to medium length (about 0.3 to about 0.7 cm.) and average in caliper (about 0.8 to about 1.1 cm. in diameter). The receptacle is urn-shaped in form. Its surface is smooth with very few hairs and with moderately thick fleshy walls. The receptacle color is between 146C and 146D sometimes lightly suffused, especially on the side exposed to the sun, with between 187B and 187A.

As the petals open (after the calyx breaks), the bud is about 2.0 to about 2.5 cm. in diameter at the widest point, about 2.8 to about 3.6 cm. in length, and ovoid to somewhat pointed in form. The color of the under surface of the newly opened petals is between 20C and 155D sometimes moderately suffused on the outermost petals with between 60A and 59B. At the point where the petal attaches, there is a large zone of between 154D and 1D. The color of the upper surfaces of the newly opened petals is between 60A and 57A. At the point where the petal attaches, there is a large zone of between 154C and 1C.

Bloom

When fully open, the bloom ranges from about 9.3 to about 13.5 cm. in diameter. Petalage is double with about 27 to 39 petals and about 3 to 13 petaloids irregularly arranged. When partially open, the bloom form is moderately high centered to somewhat cupped, and the petals are moderately tightly spiraled to somewhat cupped with petal edges somewhat reflexed outward. When fully open, the bloom form is more cupped, and the petals are loosely cupped with petal edges moderately reflexed outward to somewhat rolled.

Petals

The substance of the petals is moderately heavy and of medium thickness, with upper surfaces slightly satiny and under surfaces moderately shiny. The petals are about 4.5 to about 7.0 cm. in length and about 3.5 to about 6.5 cm. in width at the widest point. Petal margins are entire.

The outer petals are broadly obovate in shape with rounded apices to sometimes somewhat mucronate.

The inner petals are broadly obovate in shape with rounded apices to sometimes somewhat mucronate.

Petaloids are about 1.2 to about 6.1 cm. in length and about 0.8 to about 2.8 cm. in width at the widest point. Petaloids are irregularly shaped moderately oblanceolate to somewhat subulate with rounded to somewhat lacerated apices.

Newly Opened Flower

The under surface color of the outer petals is between 27D and 155C often moderately suffused near the edge with near 61B. At the point where the petal attaches, there is a large zone of near 4D. The upper surface color of the outer petals is between 61C and 66B. At the point where the petal attaches, there is a large zone of between 154D and 2D.

The under surface color of the intermediate and inner petals is between 27C and 155C often moderately suffused near the edge with near 61B. The upper surface color of the intermediate and inner petals is between 53C and 57A.

The under and upper surface colors of the petaloids are similar in coloration to the upper and under surfaces of the intermediate and inner petals.

The general tonality of the newly opened flower is between 53C and 57A.

Three-Day-Old Flower

The under surface color of the outer petals is between 155D and 155C often moderately suffused near the edge with near 64B. At the point where the petal attaches, there is a large zone of near 155A. The upper surface color of the outer petals is between 61C and 66B. At the point where the petal attaches, there is a large zone of near 150D.

The under surface color of the intermediate and inner petals is between 155D and 155C often moderately suffused near the edge with near 64B. The upper surface color of the intermediate and inner petals is between 61B and 57B.

The under and upper surface colors of the petaloids are similar in coloration to the upper and under surfaces of the intermediate and inner petals.

The general tonality of the three-day-old flower is between 61B and 57B.

On the spent bloom, the petals usually drop off cleanly.

In October in Wasco, Calif., blooms on the bush growing outdoors generally last about four to five days. Cut roses from plants grown outdoors and kept at normal indoor living temperatures generally last about four to five days.

Male Reproductive Organs

Stamens are many in number (average about 160) and are arranged regularly about the pistils; a few are mixed with petaloids. The filaments are of moderately short to medium length (about 0.4 to about 0.9 cm.) most with anthers. Filaments are between 10B and 9C in color. The anthers are moderately small for the class and all open approximately at the same time. Anther color when immature is near 22A on the external part and near 11D on the internal part. Anther color at maturity is near 164D on the external part and near 200A on the internal part. Pollen is sparse and between 18C and 20D in color.

Female Reproductive Organs

Pistils vary in number (average about 175). The styles are moderately even, average to somewhat long in length (about 0.5 to about 0.9 cm.), thin in caliper, and loosely bunched to somewhat separated. Stigma color is between 18B and 19C. Style color is between 154D and 1D usually heavily suffused near the top with between 53B and 53C. Ovaries are usually all enclosed in the calyx. The ovaries are of medium size and between 158A and 158B in color.

Hips have not been observed on this variety when grown in Wasco, Calif.

Foliage

The compound leaves are usually comprised of three to seven leaflets and are borne abundantly. The five-leaflet leaves are about 9.0 to about 14.5 cm. in length and about 8.5 to about 14.0 cm. in width at the widest point, moderately leathery to somewhat crisp in texture on both sides, and glossy in finish on the upper side and moderately glossy in finish on the under side. The leaves have a pinnate venation pattern. The terminal leaflets are about 4.3 to about 7.8 cm. in length and about 2.7 to about 5.0 cm. in width at the widest point, shaped moderately oval to somewhat ovate with moderately acuminate to somewhat acute apices and moderately acute to somewhat rounded bases. Their margins are usually simply serrate.

The upper surface color of the mature leaf is between 137A and 147A. The under surface color of the mature leaf is between 147B and 148B. The under and upper colors of the leaf veins on the mature leaf are similar in coloration to the upper and under surfaces colors of the mature leaf. The upper surface color of the young leaf is between 137B and 137A, usually heavily suffused with between 187B and 187A. The under surface color of the young leaf is between 147B and 148B, usually heavily suffused with between 187B and 187A. The under and upper colors of the leaf veins on the young leaf are similar in coloration to the upper and under surfaces colors of the young leaf.

The rachis is about 2.4 to about 5.8 cm. in length, about 0.1 to about 0.2 cm in width at the widest point, and somewhat rough. The upper side is deeply grooved with few hairs and stipitate glands on the edges of the grooves. The under side of the rachis is somewhat rough with very few stipitate glands and small prickles. The rachis color is near 146D on the under side and near 137B on the upper side, often moderately suffused on the young leaves with between 187B and 187A.

The stipules are about 1.2 to about 2.4 cm. in length and of medium to somewhat wide width (about 0.5 to about 0.9 cm.) with medium to somewhat long straight points that usually turn out at an angle of more than 45 degrees and sometimes recurve toward the stem. The under and upper surface color of the stipule is between 139A and 137A sometimes lightly suffused on the young leaves with between 187B and 187A. The upper and under surfaces of the stipules are smooth in texture.

The petiole is moderately light to average in caliper and somewhat rough. The upper side is deeply grooved with few hairs and stipitate glands on the edges of the grooves. The under side of the petiole is somewhat rough with very few stipitate glands and small prickles. The petiole is about 0.6 to about 1.7 cm. in length and about 0.1 to about 0.2 cm in width at the widest point. The petiole color is near 146D on the under side and near 137B on the upper side, often moderately suffused on the young leaves with between 187B and 187A.

The plant displays an above average degree of resistance to powdery mildew (*Sphaerotheca pannosa*) and rust (*Phragmidium* sp.) and an average degree of resistance to downy mildew (*Peronospora sparsa*) as compared to other commercial varieties grown under comparable conditions in Wasco, Calif. The plant's winter hardiness and drought/heat tolerance are yet to be determined.

Growth

The plant has an upright moderately spreading medium height growing habit (about 100 to about 140 cm. in height and about 122 to about 150 cm. spread at the widest point), with full branching. It displays vigorous growth and the canes are of somewhat light to medium sized caliper for the class (about 1.1 to about 2.2 cm. in diameter at the widest point).

The color of the major stems is between 146A and 146B. The major stems are rough in texture and they bear some large prickles that are about 0.8 to about 1.4 cm. in length. The large prickles are almost straight, angled slightly downward with a moderately short somewhat broad oval base; prickle color is between 164B and 165C. The major stem bears few small prickles of similar shape and coloration.

The color of the branches is between 146B and 146A. The branches are rough in texture and they bear few large prickles which are of similar size and shape to the large prickles on the major stems; prickle color is near 148B. The branches bear very few small prickles of similar shape and coloration.

The color of the new shoots is between 146B and 146A often moderately suffused with between 187C and 187B. The new shoots are rough in texture and they bear few large prickles which are of similar size and shape to the large prickles on the major stems; prickle color is between 148B and 147C usually heavily suffused with between 187C and 187D. The shoots bear very few small prickles of similar shape and coloration.

I claim:

1. A new and distinct Hybrid Tea rose plant of the variety designated 'WEKmamoprela' substantially as described and illustrated herein.

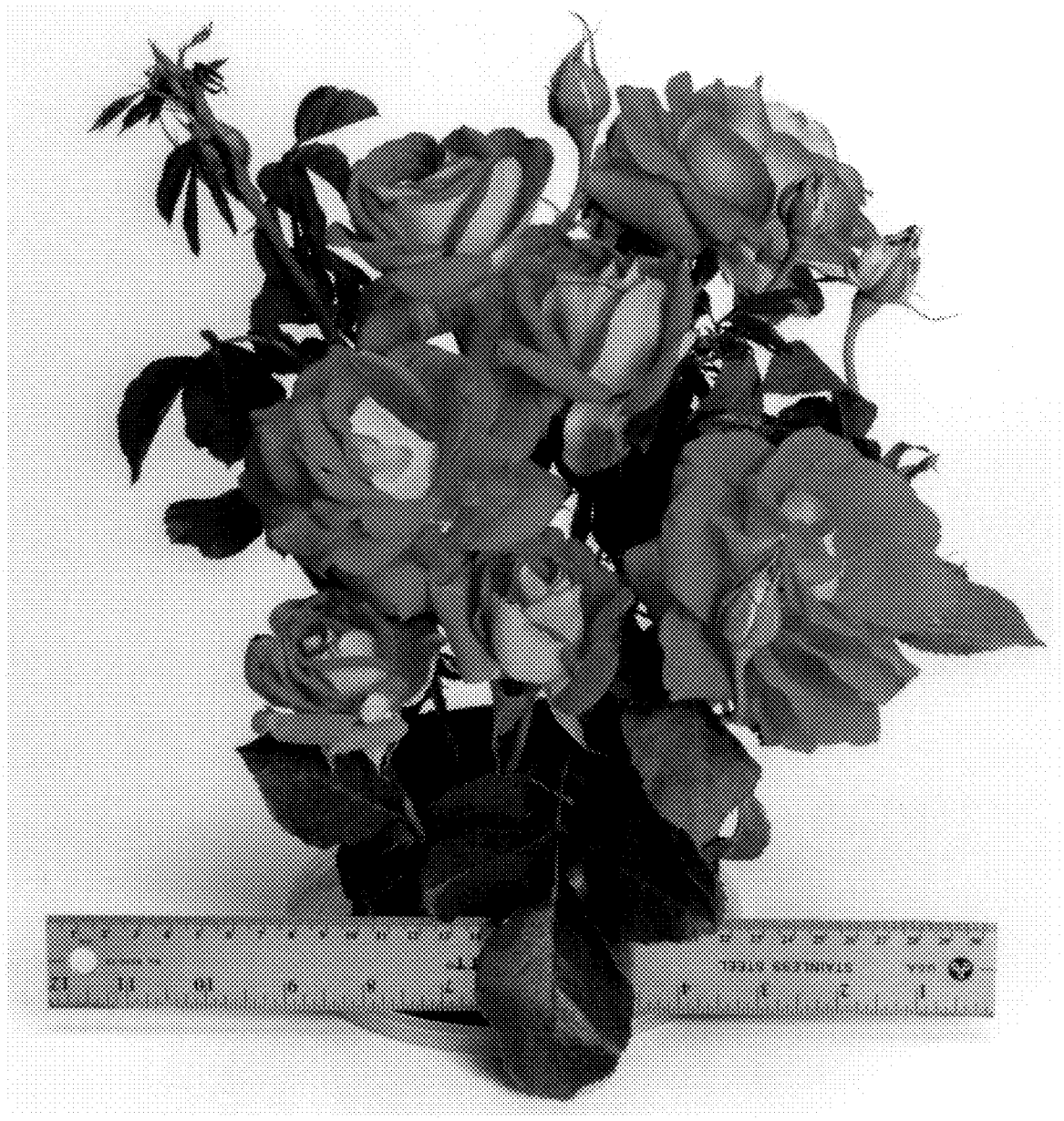

* * * * *